(12) United States Patent
Takimoto

(10) Patent No.: US 9,839,710 B1
(45) Date of Patent: Dec. 12, 2017

(54) CHLORINE DIOXIDE GAS GENERATOR

(71) Applicant: TAKIMOTOGIKEN KOGYO CO., LTD., Nagoya (JP)

(72) Inventor: Masateru Takimoto, Nagoya (JP)

(73) Assignee: TAKIMOTOGIKEN KOGYO CO., LTD., Nagoya (JP)

( * ) Notice: Subject to any disclaimer, the term of this patent is extended or adjusted under 35 U.S.C. 154(b) by 0 days.

(21) Appl. No.: 15/495,566

(22) Filed: Apr. 24, 2017

(30) Foreign Application Priority Data

Dec. 8, 2016 (JP) ................................. 2016-238092

(51) Int. Cl.
*A61L 2/20* (2006.01)
*B01D 19/00* (2006.01)
*C01B 11/02* (2006.01)

(52) U.S. Cl.
CPC ............ *A61L 2/20* (2013.01); *B01D 19/0005* (2013.01); *B01D 19/0047* (2013.01); *C01B 11/024* (2013.01); *A61L 2202/11* (2013.01); *A61L 2202/25* (2013.01)

(58) Field of Classification Search
CPC ..... A61L 2/18; A61L 2/20; A61L 2/26; A61L 2202/11; A61L 2202/25; B01D 19/0047; B01D 19/0005; C01B 11/024
See application file for complete search history.

(56) References Cited

U.S. PATENT DOCUMENTS 1,765,087 A * 6/1930 Mase ....................... B01D 3/18
261/114.1
4,234,446 A * 11/1980 Ramras ...................... B01J 7/02
252/187.21
4,456,510 A 6/1984 Murakami et al.
(Continued)

FOREIGN PATENT DOCUMENTS

| GB | 2004475 A | 9/1978 |
|----|-----------|--------|
| GB | 2146912 A | 5/1985 |
| JP | 4942643 | 11/1974 |

(Continued)

OTHER PUBLICATIONS

Japan Patent Office. Notification of Reasons of Refusal for Patent Application No. 2014-063873 dated Jun. 2, 2014 (English translation).

*Primary Examiner* — Timothy Cleveland
(74) *Attorney, Agent, or Firm* — Trego, Hines & Ladenheim, PLLC

(57) ABSTRACT

A chlorine dioxide gas generator (100) is provided which capable of efficiently generating and gasifying a chlorine dioxide solution within a short period of time without accidental leakage, facilitating fumigation, and facilitating washing of the interior of the generator within a short period of time. The chlorine dioxide gas generator (100) includes a separation tank (20) that separates a chlorine dioxide gas (30*b*) from a chlorine dioxide solution (30*a*) generated in the reactor (10), the separation tank (20) including a separation cylinder (21), downwardly convex trays (22), upwardly convex tray covers (23), nubs (24) packed between the trays (22) and tray covers (23), a liquid supply pipe (25) communicating with an upper portion of the separation cylinder (21), and an air-mixture cylinder (27) that forms an air-mixture space (27*a*) around the separation cylinder (21) on a waste liquid chamber (26).

1 Claim, 9 Drawing Sheets

(56) References Cited

U.S. PATENT DOCUMENTS

| | | | |
|---|---|---|---|
| 4,851,198 A | 7/1989 | Lohrberg | |
| 9,446,160 B2 | 9/2016 | Takimoto | |

FOREIGN PATENT DOCUMENTS

| | | | |
|---|---|---|---|
| JP | 54-153468 U | 10/1979 | |
| JP | 10182106 H | 7/1998 | |
| JP | 10192377 H | 7/1998 | |
| JP | 2010207539 A | 9/2010 | |
| JP | 2012011028 A | 1/2012 | |
| JP | 2015182949 A | 10/2015 | |

\* cited by examiner

CHLORINE DIOXIDE GAS GENERATOR

BACKGROUND OF THE INVENTION

Field of the Invention

The present invention relates to a chlorine dioxide gas generator for disinfecting an enclosed space using chlorine dioxide gas.

Description of the Related Art

Various kinds of fumigation devices that use chlorine dioxide gas have been proposed for example in Japanese Unexamined Patent Application Publication No. 1998-192377 and in Japanese Unexamined Patent Application Publication No. 2010-207539, and various solutions to the disadvantages of the use of chlorine dioxide gas have been developed. Typical disadvantages of the use of chlorine dioxide gas are listed below:
(i) Since chlorine dioxide gas is unstable and may explode, it must be used with caution for short periods of time.
(ii) Chlorine dioxide gas cannot be stored for a long time, and therefore needs to be generated at the site of use.
(iii) When a first chemical containing chlorite and a second chemical containing an acid react with each other, chlorine dioxide gas is generated as an aqueous solution. Therefore, in order to use the gas for fumigation, it must first be separated from the solution.

The contents of Japanese Unexamined Patent Application Publication No. 1998-192377 and Japanese Patent No. 5639294 are incorporated herein by reference in their entirety.

SUMMARY OF THE INVENTION

Problems to be Solved by the Invention

JP1998-192377 describes an invention relating to a method and an apparatus for generating chlorine dioxide gas, which has an object of providing a method for simply and safely generating chlorine dioxide gas, capable of efficiently generating chlorine dioxide gas in order to carry out fumigation, and an apparatus for generating chlorine dioxide gas. As shown in FIG. 8 (corresponding to FIG. 1 of JP1998-192377), such a method and apparatus for generating chlorine dioxide gas may include, for example: "Stirring a mixed solution containing a nonvolatile organic acid solution, a chlorite solution and a chloride for improving chlorine dioxide-producing ability. This gas generator is equipped with a reaction vessel 1, an air pump 3, a vent pipe 6 which communicates with the air pump 3 and an air stone 7. The air stone 7 is immersed in the mixed solution and a sealable opening part 1a is formed at the top of the reaction vessel 1 at a position higher than the water level of the mixed solution."

In this way, the "method and apparatus for generating chlorine dioxide gas" described in JP1998-192377 is thought to be capable of "providing a method for simply and safely generating chlorine dioxide gas, capable of efficiently generating chlorine dioxide gas in order to carry out fumigation disinfection", thus solving the foregoing problems (i) to (iii).

However, paragraph [0021] of JP1998-192377 discloses the following: "Specifically, the container filled with the above-mentioned liquid mixture and an agitator or a bubbling apparatus may be carried into the disinfection environment, where stirring or bubbling may be performed. Thus generated chlorine dioxide gas, which in the case of bubbling is concomitant with a bubbling gas, diffuses out of the reaction solution (inside of the disinfection environment), thus realizing the desired fumigation disinfection of the disinfection environment." According to this description in conjunction with FIG. 8, it is understood that in the method and apparatus for generating chlorine dioxide gas described in JP1998-192377, there is a risk that chlorine dioxide gas will be generated before starting the bubbling process, such as when filling the container with the liquid mixture or when carrying the container into the disinfection environment.

In view of the above, the inventors of the present invention made the invention described in JP5639294, to provide a chlorine dioxide gas generator that could achieve two objectives: to efficiently generate chlorine dioxide gas within a short period of time without accidental leakage and make the fumigation process easy to control, and to efficiently separate the chlorine dioxide gas from the water.

The invention described in JP5639294 had a basic configuration of "a chlorine dioxide gas generator including a reactor which causes a reaction between a first chemical containing chlorite and a second chemical containing acid, and a separation tank which separates a chlorine dioxide gas from a chlorine dioxide solution generated in the reactor, the chlorine dioxide gas generator being adapted to disinfect an enclosed space by means of the chlorine dioxide gas, the separation tank further including a plurality of vertically arranged gas discharge chambers, a plurality of drain pipes provided between the mutually adjacent gas discharge chambers, a liquid supply pipe which feeds the chlorine dioxide solution from the reactor to an uppermost gas discharge chamber, and an air supply pipe which feeds air into each of the gas discharge chambers", whereby air was fed into each of the gas discharge chambers through the air supply pipe while the chlorine dioxide solution flowed from the liquid supply pipe into the gas discharge chambers through the drain pipes, to separate chlorine dioxide gas into the air in each of the gas discharge chambers.

Although the invention described in JP5639294 did simultaneously solve the aforementioned problems (i) to (iii), later consideration by the inventors lead to the discovery that continuously forming a plurality of gas discharge chambers was unfortunately costly and time-consuming, and not suitable for mass production. Moreover, in this type of apparatus, chlorine dioxide solution and chlorine dioxide gas can easily remain inside the apparatus after use, which left unattended could possibly lead to chlorine dioxide gas leaking out and harming the environment. It is therefore necessary to wash the inside of the apparatus with water after use, but it was revealed that since the invention described in JP5639294 has a plurality of gas discharge chambers formed continuously, washing the apparatus is troublesome.

In other words, when performing fumigation using this chlorine dioxide gas, in addition to the aforementioned disadvantages (i) to (iii), a new issue has been recognized, namely:
(iv) After performing fumigation using chlorine dioxide gas, there is a need to facilitate washing so that no chlorine dioxide solution or gas remains inside the apparatus.

In view of the above, the present invention was made as a result of due consideration of how to make an apparatus for handling the hazardous material of chlorine dioxide gas more efficient and safe.

It is thus an object of the present invention to provide a chlorine dioxide gas generator that is capable of:

(1) Efficiently generating chlorine dioxide solution and gasifying the solution within a short period of time without accidental leakage, and facilitating fumigation work.
(2) Achieving objective (1) above and efficiently separating chlorine dioxide gas from the chlorine dioxide solution.
(3) Facilitating washing of the interior of the gas generator within a short period of time.

Means of Solving the Problems

In order to solve the aforementioned problems, the means employed by the present invention will be described using the reference numerals used in the description of the embodiments below:

"A chlorine dioxide gas generator 100 comprising:
a reactor 10 configured to cause a reaction between a first chemical containing chlorite and a second chemical containing acid; and
a separation tank 20 configured to separate a chlorine dioxide gas 30b from a chlorine dioxide solution 30a generated in the reactor 10, the chlorine dioxide gas generator 100 being adapted to disinfect an enclosed space 40 by means of the chlorine dioxide gas 30b,
wherein the separation tank 20 comprises:
a separation cylinder 21 provided standing on a waste liquid chamber 26 so as to enclose holes 26a provided at the center of the waste liquid chamber 26, the separation cylinder 21 having holes 21a at its upper portion;
a plurality of trays 22 having edges 22a connected to an inner surface of the separation cylinder 21, each tray 22 being of a downwardly convex shape and having holes 22b at its center portion;
a plurality of tray covers 23, each tray cover 23 being arranged at a predetermined distance from a respective tray 22, each tray cover 23 being of an upwardly convex shape and having an edge 23a that is separate from the inner surface of the separation cylinder 21 so as to form a passage;
a plurality of nubs 24 arranged between the plurality of trays 22 and the plurality of tray covers 23;
a liquid supply pipe 25 from the reactor 10 communicating with the upper portion of the separation cylinder 21; and
an air-mixture cylinder 27 arranged on the waste liquid chamber 26 and configured to form an air-mixture space 27a around the separation cylinder 21, the air-mixture cylinder 27 having at its top end a water supply port 27b, and having on its sides an air-mixture discharge port 27c and an air supply port 27d configured to supply air from a blower fan 50."

To summarize, the chlorine dioxide gas generator 100 according to an embodiment of the present invention, as shown in FIG. 1, releases a diluted chlorine dioxide gas 30b in an enclosed space 40, for example a factory, an office building, or an ordinary house, in order to disinfect the enclosed space 40. There are two types of this chlorine dioxide gas generator 100: A direct type which directly emits the diluted chlorine dioxide gas 30b within the enclosed space 40 as shown on the left side of FIG. 1 (the generator being located inside the building), and a feed type which utilizes the outside air to dilute the chlorine dioxide gas 30b, and feeds the resultant diluted chlorine dioxide gas 30b into the enclosed space 40 as shown on the right side of FIG. 1 (the generator being located outside the building).

The chlorine dioxide gas generator 100 shown in FIGS. 2 and 3 includes a reactor 10 that makes a first chemical containing chlorite and a second chemical containing acid react with each other, and a separation tank 20 that separates chlorine dioxide gas from a chlorine dioxide solution generated in the reactor 10.

Various types of reactors can be used as the reactor 10 that makes the first and second chemical react with each other. An embodiment described later employs, as shown in FIGS. 6 and 7, a reactor 10 including a large cylinder 11 in the shape of a cylinder having a bottom surface, which makes up the external shape of the reactor 10, a medium cylinder 12 in the shape of a cylinder having a bottom surface and housed within the large cylinder 11, and a small cylinder 13 in the shape of a cylinder having a bottom surface and housed within the medium cylinder 12, in which, as shown in FIG. 6, a first spiral groove 14a is formed between the large cylinder 11 and the medium cylinder 12, and a second spiral groove 14b is formed between the medium cylinder 12 and the small cylinder 13. As shown in FIG. 7, a lid 15 is mounted to the large cylinder 11 which sequentially houses the medium cylinder 12 and the small cylinder 13, the lid 15 securing the medium cylinder 12 and the small cylinder 13 within the large cylinder 11.

As shown in FIGS. 2 to 4, the chemicals in a first chemical tank 16a and a second chemical tank 16b are separately fed to the reactor 10 through chemical transporting pumps 16c, and are respectively fed to a first connection port 11a and a second connection port 11b of the large cylinder 11, as shown in FIG. 6. In other words, the chemicals in the first chemical tank 16a and the second chemical tank 16b are contained separately respectively in the first chemical tank 16a and the second chemical tank 16b, and thus will not accidentally react with each other before they are fed to the reactor 10.

As a result, generation of the chlorine dioxide solution 30a in the reactor 10 will not occur unless the chemicals are fed into the small space constituting this reactor 10, which means that not only will there not be any accidental generation of the chlorine dioxide gas 30b, but also that by controlling the feeding of the chemicals, the amount of gas and time of generation can be controlled. Due to the presence of this reactor 10, the chlorine dioxide gas generator 100 according to an embodiment of the present invention can be made much smaller and compact than for example the apparatus proposed in JP 1998-192377.

The generated chlorine dioxide solution 30a is transported from an outlet 15a of the lid 15 that seals the interior of the reactor 10, as shown in FIG. 7, to the separation tank 20 through a hose or the like, and the chlorine dioxide gas 30b is separated in this separation tank 20. In a chlorine dioxide gas generator 100 of the direct type shown in the left side of FIG. 1, the separated chlorine dioxide gas 30b is sprayed, as indicated by the arrows in the figure, into the enclosed space 40 in which the chlorine dioxide gas generator 100 is installed.

As shown in FIGS. 4 and 5, the separation tank 20 includes a separation cylinder 21, trays 22, tray covers 23, nubs 24, a liquid supply pipe 25, and an air-mixture cylinder 27. As shown in FIG. 5 (a), air fed from holes 26a of a waste liquid chamber 26 via a compressor 29 is fed to the separation cylinder 21 from below, and chlorine dioxide solution 30a generated in the reactor 10 is fed to the separation cylinder 21 from above, such that separation of chlorine dioxide gas 30b from the chlorine dioxide solution 30a and dilution of the chlorine dioxide gas 30b with air occur simultaneously. When washing the interior of the separation tank 20, washing is carried out as shown in FIG. 5 (b), by stopping feeding of chlorine dioxide solution 30a from the liquid supply pipe 25 of the reactor 10 and feeding washing water from a water supply port 27b described later, and air from the holes 26a of the waste liquid chamber 26 via the compressor 29.

The separation cylinder 21 constituting the separation tank 20 is provided standing on top of the waste liquid chamber 26 and enclosing holes 26a at the center of the waste liquid chamber 26, and has holes 21a at its upper portion. The separation cylinder 21 supports the trays 22 and tray covers 23 described later, and houses the nubs 24. In addition, the lower side of the interior of the separation cylinder 21 is fed with air from the holes 26a of the waste liquid chamber 26 via the compressor 29, and this air rises through a series of complex passages formed by the holes 22 of the trays 22, the gaps between the nubs 24, and the passages between the edges 23a of the tray covers 23 and the inner surface of the separation cylinder 21.

Meanwhile, as described above, the upper side of the interior of the separation cylinder 21 is fed with the chlorine dioxide solution 30a from the liquid supply pipe 25 of the reactor 10, or with washing water from the water supply port 27b. The chlorine dioxide solution 30a or washing water flows downwardly onto the top surfaces of the tray covers 23, passes through the passages between the edges 23a of the tray covers 23 and the inner surface of the separation cylinder 21 and the gaps between the nubs 24 and is caught in the trays 22, and then flows further down through holes 22b of the trays 22 until it finally flows into the waste liquid chamber 26 through the holes 26a.

As shown in an enlarged view in FIG. 5 (a), each tray 22 is of a downwardly convex shape and has an edge 22a connected to the inner surface of the separation cylinder 21 and holes 22b at its center. The trays 22 are made in this downwardly convex shape in order to allow for accumulation of up to a certain amount of chlorine dioxide solution 30a or washing water provided from above, and gather the accumulated chlorine dioxide solution 30a or washing water in the center to let it flow down through the holes 22b. These holes 22b are provided at the center of the tray 22 in order to make the chlorine dioxide solution 30a or washing water caught by the tray 22 flow down through the holes 22b onto the center of the top surface of the below tray cover 23 and create the longest possible flow path through the passage between the edge 23a of the tray cover 23 and the inner surface of the separation cylinder 21, so as maximize the contact time and area of the chlorine dioxide solution 30a with the air, or the washing water with the surfaces of each member.

Also shown in an enlarged view in FIG. 5 (a), each tray cover 23 is located at a predetermined distance from each tray 22, and is of an upwardly convex shape having and edge 23a separated from the inner surface 21 of the separation cylinder 21 to form a passage. The tray covers 23 are made in this upwardly convex shape in order to make the chlorine dioxide solution 30a or washing water flow into the passage between the edge 23a of the tray cover 23 and the inner surface of the separation cylinder 21, so as to maximize the contact time and area of the chlorine dioxide solution 30a with the air, or the washing water with the surfaces of each member.

As shown in FIG. 5 (a), the nubs 24 packed between the tray covers 23 and respective trays 22 make the flow path of the chlorine dioxide solution 30a or the washing water as long and complex as possible, and can be made of a material that is not corroded by the chlorine dioxide solution 30a or chlorine dioxide gas 30b, for example thin metal pieces or Teflon™.

Further, the top of the interior of the separation cylinder 21 configured as described above is in communication with the liquid supply pipe 25 of the reactor 10 and the water supply port 27b that feeds washing water from a water supply not shown here, allowing for chlorine dioxide solution 30a or washing water to be fed into the separation cylinder 21.

The air-mixture cylinder 27 is provided on top of the waste liquid chamber 26 and around the separation cylinder 21, as shown in FIGS. 2 to 4. As shown in FIG. 4, this air-mixture cylinder 27 forms an air-mixture space 27a around the separation cylinder 21. At the top end of the air-mixture cylinder 27 there is formed the aforementioned water supply port 27b, and at the sides of the air-mixture cylinder 27 there are formed an air-mixture discharge port 27c and an air supply port 27d which feeds air from a blower fan 50. In other words, when chlorine dioxide gas 30b that has been separated from the chlorine dioxide solution 30a in the separation cylinder 21 is fed into the air-mixture space 27a through the holes 21a formed at the upper portion of the separation cylinder 21, the air-mixture cylinder 27 allows the chlorine dioxide gas 30b to be diluted with air fed into the air-mixture space 27a from the air supply port 27d of the blower fan 50 and fed into the enclosed space 40 through the air-mixture discharge port 27c formed at the side of the air-mixture cylinder 27.

The waste liquid chamber 26 is provided below the separation tank 20 configured as described above. This waste liquid chamber 26 may be of any configuration, so long as it has holes 26a in communication with the interior of the separation tank 20, and provided that these holes 26a can let chlorine dioxide solution 30a from which chlorine dioxide gas 30b has not been completely extracted flow down into the waste liquid chamber 26 for storage as waste liquid, and feed air that has been fed by the compressor 29 into the waste liquid chamber 26 into the separation tank 20.

In the chlorine dioxide gas generator 100 configured as described above, according to an embodiment described later, specific materials are fed into the reactor 10 to continuously generate chlorine dioxide solution 30a, this chlorine dioxide solution 30a is fed into the separation tank 20 through the liquid supply pipe 25, and the compressor 29 is activated to feed air into the waste liquid chamber 26, which air is fed into the separation tank 20 through the holes 26a of the waste liquid chamber 26, as shown in FIG. 5 (a). In other words, chlorine dioxide 30a is fed into the separation tank 20 from above while, at the same time, air for separating and diluting chlorine dioxide gas 30b from the chlorine dioxide solution 30a is fed into the separation tank 20 from below. In this manner, as will be described in further detail below, chlorine dioxide gas 30b is separated from the chlorine dioxide solution 30a and diluted with air inside the air-mixture space 27a, and is then fed into the enclosed space 40 through the air-mixture discharge port 27c of the air-mixture cylinder 27.

When separating chlorine dioxide gas 30b in the separation tank 20, there is virtually no need to adjust the pressure at which the chlorine dioxide solution 30a is fed, or the pressure of the air from the compressor 29 fed into the waste liquid chamber 26. This is because the chlorine dioxide solution 30a is fed into the separation tank 20 through the liquid supply pipe 25 and then flows downwardly due to its own weight, while the air fed into the waste liquid chamber 26 is fed by the compressor 29 into the separation tank 20 and then rises through the chlorine dioxide solution 30a due to buoyancy. The respective pressures can therefore be set to any suitable value.

As shown in FIG. 5 (a), the chlorine dioxide solution 30a fed into the separation tank 20 from above falls onto the upwardly convex surfaces of the tray covers 23, flows across the surfaces of the tray covers 23 in every direction, and then flows downwardly through the passages formed between the edges 23a of the tray covers 23 and the inner surface of the separation cylinder 21. Since the nubs 24 are arranged below each tray cover 23, the chlorine dioxide solution 30a flows into the complex passages formed by the nubs 24, and is then caught by the tray 22 located below. The chlorine dioxide solution 30a fed into the separation tank 20 from the liquid supply pipe 25 will thus flow through the complex passages formed by the tray covers 23, the nubs 24, and the trays 22, flowing a distance that is several times longer than if the solution had been falling freely. The chlorine dioxide solution 30a will naturally also collide with the nubs 24, the trays 22, and the tray covers 23, and the impact of such collisions facilitates the emission of chlorine dioxide gas 30b.

The air fed into the separation tank 20 from below through the holes 26a of the waste liquid chamber 26 will also rise up through the complex passages formed by the nubs 24 through the holes 22b of the trays 22. At this time, the aforementioned chlorine dioxide solution 30a will come into contact with the rising air, causing chlorine dioxide gas 30b to be separated from the chlorine dioxide solution 30a and diluted by the rising air. In other words, the air entering the air-mixture cylinder 27 through the holes 21a of the separation cylinder 21 will be mixed with separated chlorine dioxide gas 30b.

Further, as shown in FIG. 5 (b), by feeding washing water into the separation tank 20 from the water supply port 27b instead of the chlorine dioxide solution 30a, and feeding air into the separation tank 20 from the waste liquid chamber 26, any residual chlorine dioxide solution 30a in the trays 22, on the surfaces of the tray covers 23, or in the passages between the nubs 24 can be washed off, and any residual chlorine dioxide remaining in the washed off waste liquid can be separated into the air by way of the complex passages and stimulation by the air. In other words, apart from washing of the separation tank 20, this washing process using washing water also allows residual chlorine dioxide to be discharged, and since it is enough to forcibly feed water into the separation tank 20 from the water supply port 27b, washing of the interior of the separation tank 20 can be carried out in a very short time.

Since air is also fed by the compressor 29 into the waste liquid in the waste liquid chamber 26 during the aforementioned washing process in a so-called bubbling operation, residual chlorine dioxide in the waste liquid is gasified and fed into the enclosed space 40 via the air-mixture discharge port 27c. Of course, the waste liquid in the waste liquid chamber is later safely treated by an apparatus not shown here to yield waste water that is substantially free of chlorine dioxide.

Effects of the Invention

The chlorine dioxide gas generator 100 according to an embodiment of the present invention achieves the following:
(i) Chlorine dioxide gas, which is unstable and may explode, can be used for fumigation in a safe manner and within a short period of time.
(ii) Chlorine dioxide gas, which cannot be stored for a long time, can be generated at the site of use.
(iii) Chlorine dioxide gas can be separated from a generated chlorine dioxide solution.
(iv) The chlorine dioxide gas generator can be washed after performing fumigation using chlorine dioxide gas, so that no chlorine dioxide remains inside the generator.

DETAILED DESCRIPTION OF THE EMBODIMENTS

Figure 1:
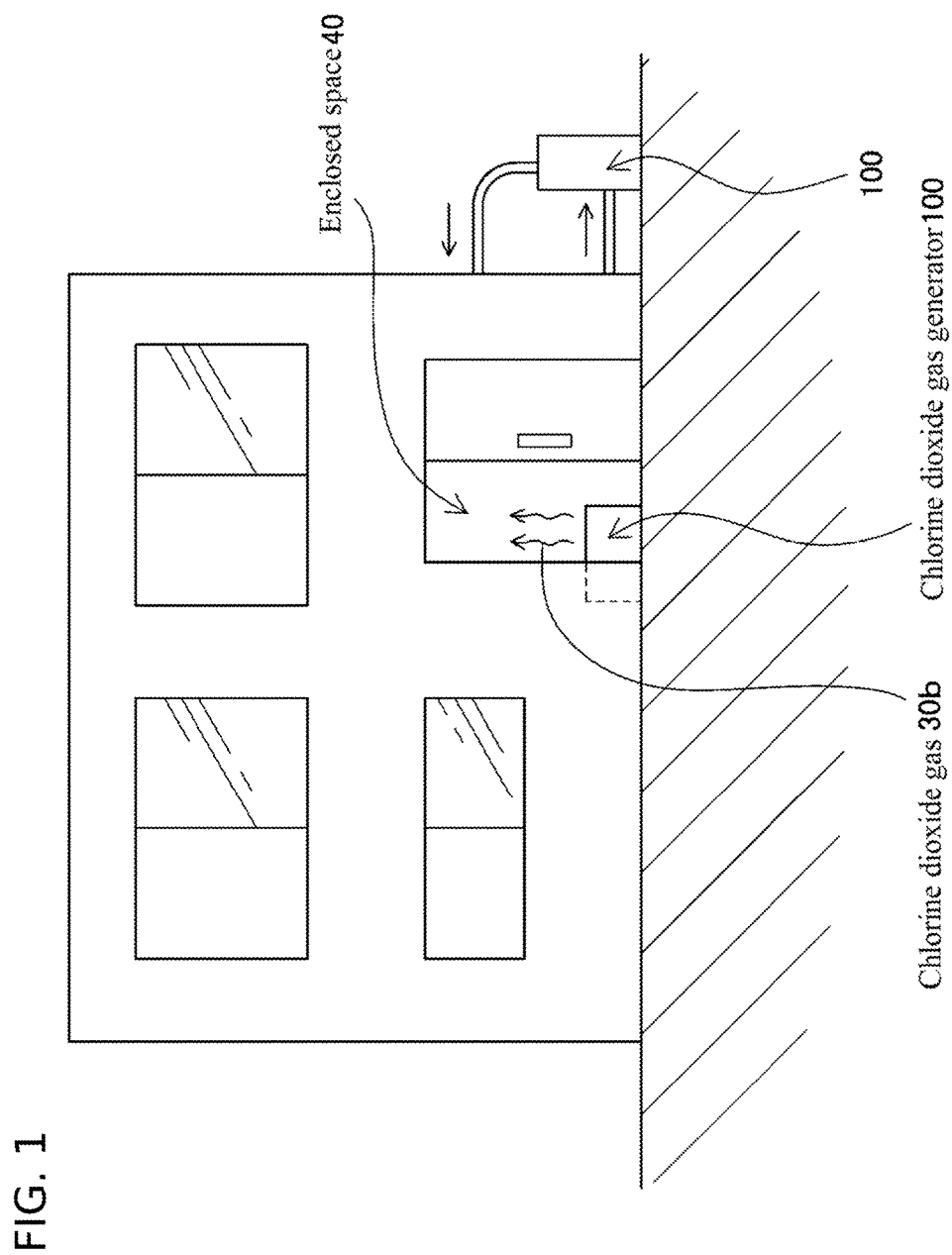
FIG. 1 is a front view of an enclosed space 40 showing fumigation of the interior of the enclosed space 40 being performed using the chlorine dioxide gas generator 100 according to an embodiment of the present invention.

The invention having the aforementioned construction will now be described with reference to the embodiments of the chlorine dioxide gas generator 100 shown in the drawings. As shown in FIG. 1, the chlorine dioxide gas generator 100 emits the chlorine dioxide gas 30b in an enclosed space 40 such as a factory, an office building, or an ordinary house, and disinfects the enclosed space 40 by means of the chlorine dioxide gas 30b. There are two types of embodiments of the chlorine dioxide gas generator 100; a direct type as shown on the left side of FIG. 1, which directly emits the chlorine dioxide gas 30b inside the enclosed space 40, and a feed type as shown on the right side of FIG. 1 (installed outside the building), which uses air from outside the enclosed space 40 to dilute the chlorine dioxide gas 30b and feeds the diluted chlorine dioxide gas 30b into the enclosed space 40.

Figure 2:
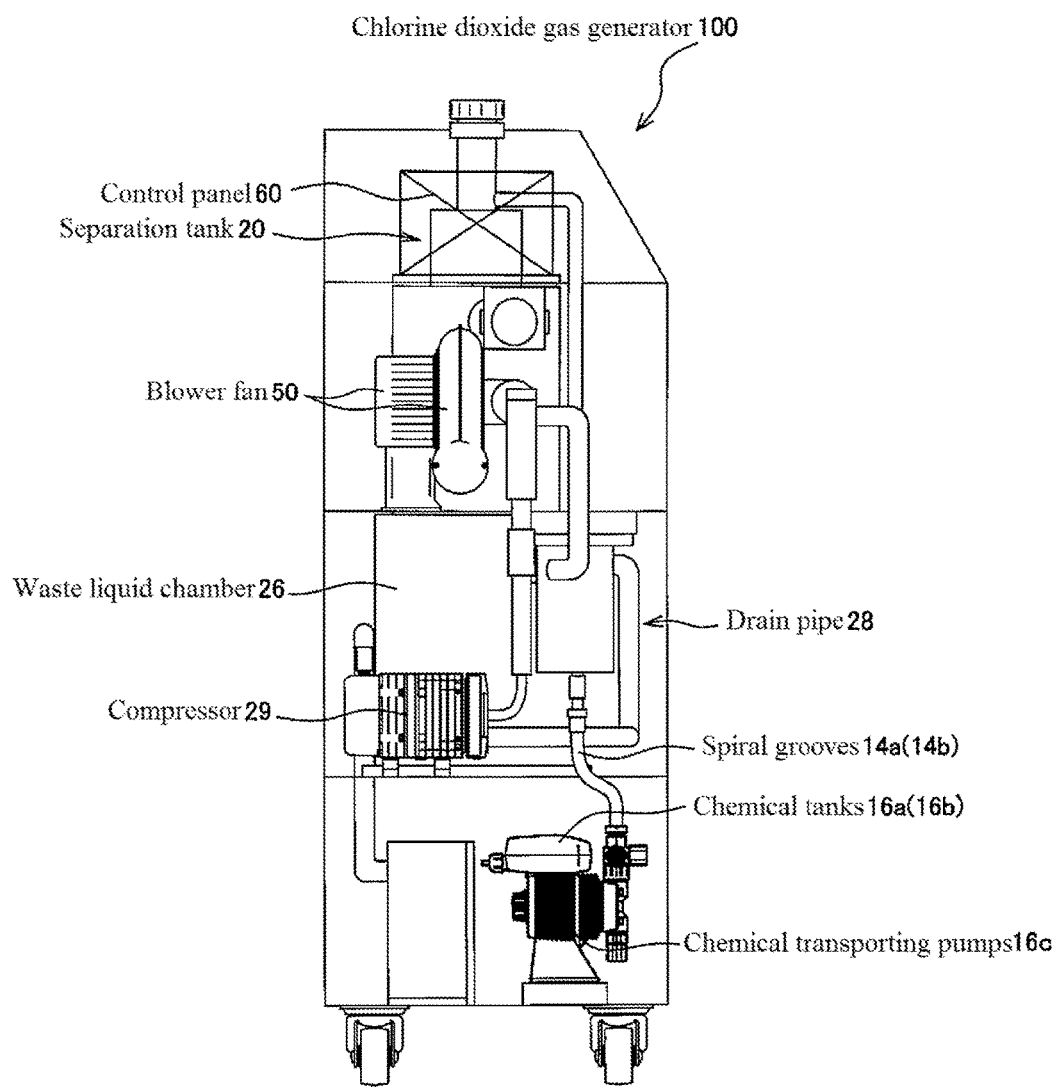
FIG. 2 is a side view of a separation tank 20 of the chlorine dioxide gas generator 100.
Figure 3:
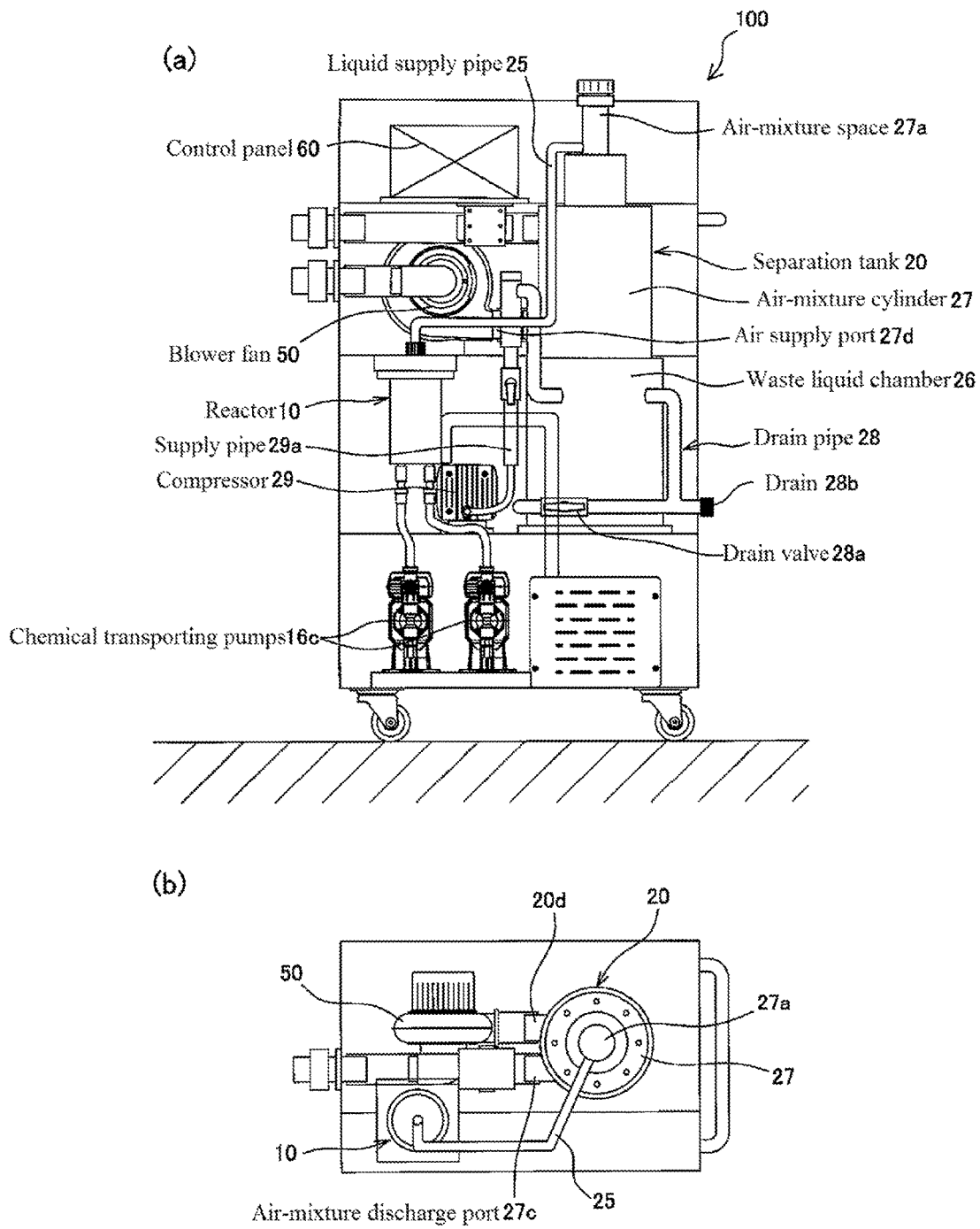
FIG. 3 shows the separation tank 20, where (a) is a front view and (b) is a planar view.

As shown in FIGS. 2 to 3, the chlorine dioxide gas generator 100 according to the present embodiment includes a reactor 10 which causes a reaction between a first chemical containing chlorite and a second chemical containing acid to generate a chlorine dioxide solution 30a, and a separation tank 20 which separates a chlorine dioxide gas 30b from the chlorine dioxide solution 30a generated in the reactor 10.

Figure 6:
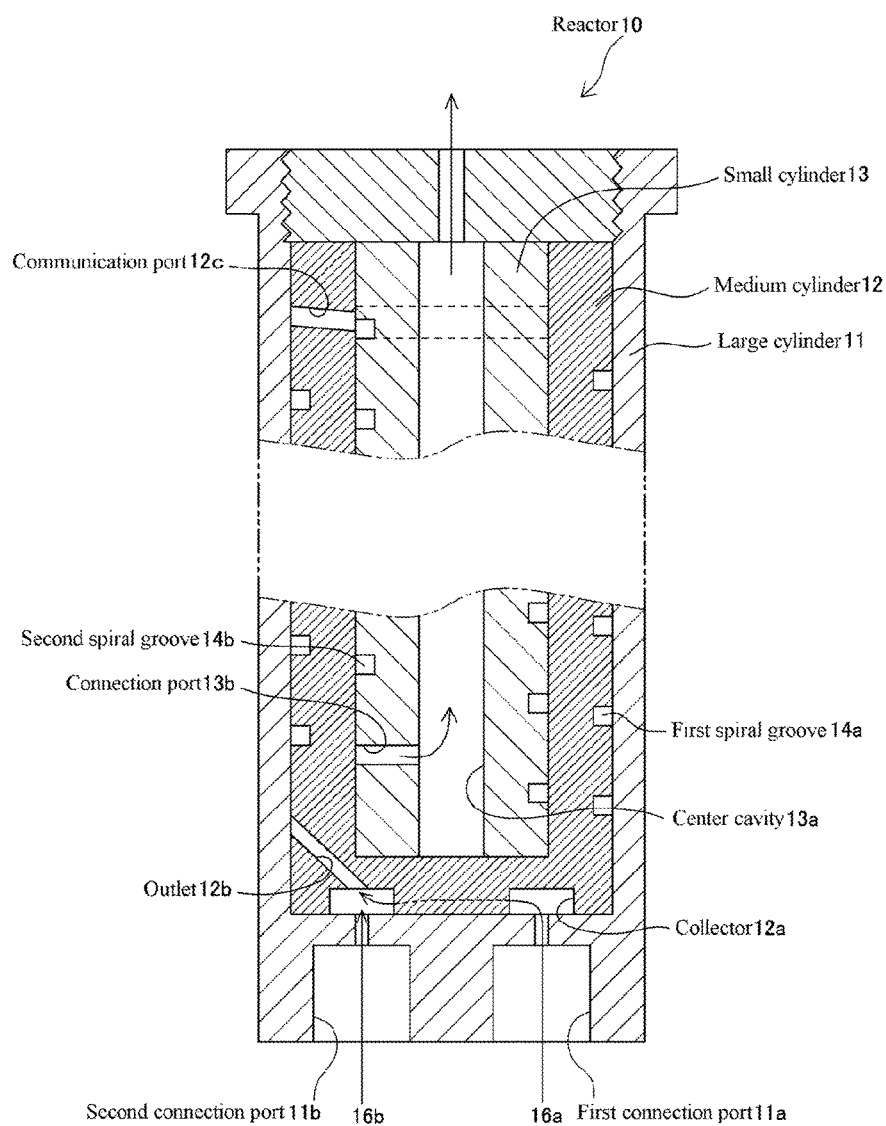
FIG. 6 is a schematic cross-sectional view of a reactor 10 used in the chlorine dioxide gas generator 100.
Figure 7:
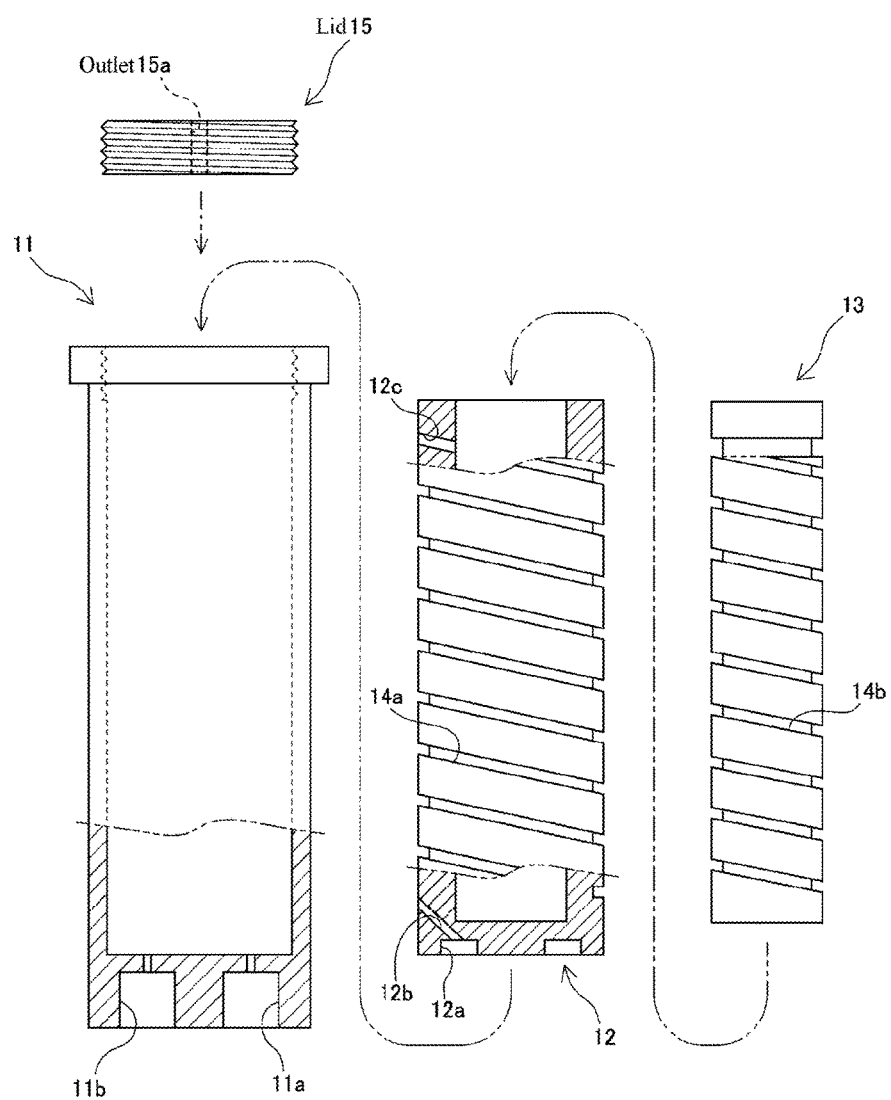
FIG. 7 is a front view showing sectional views of the disassembled components of the reactor 10.
Figure 8:
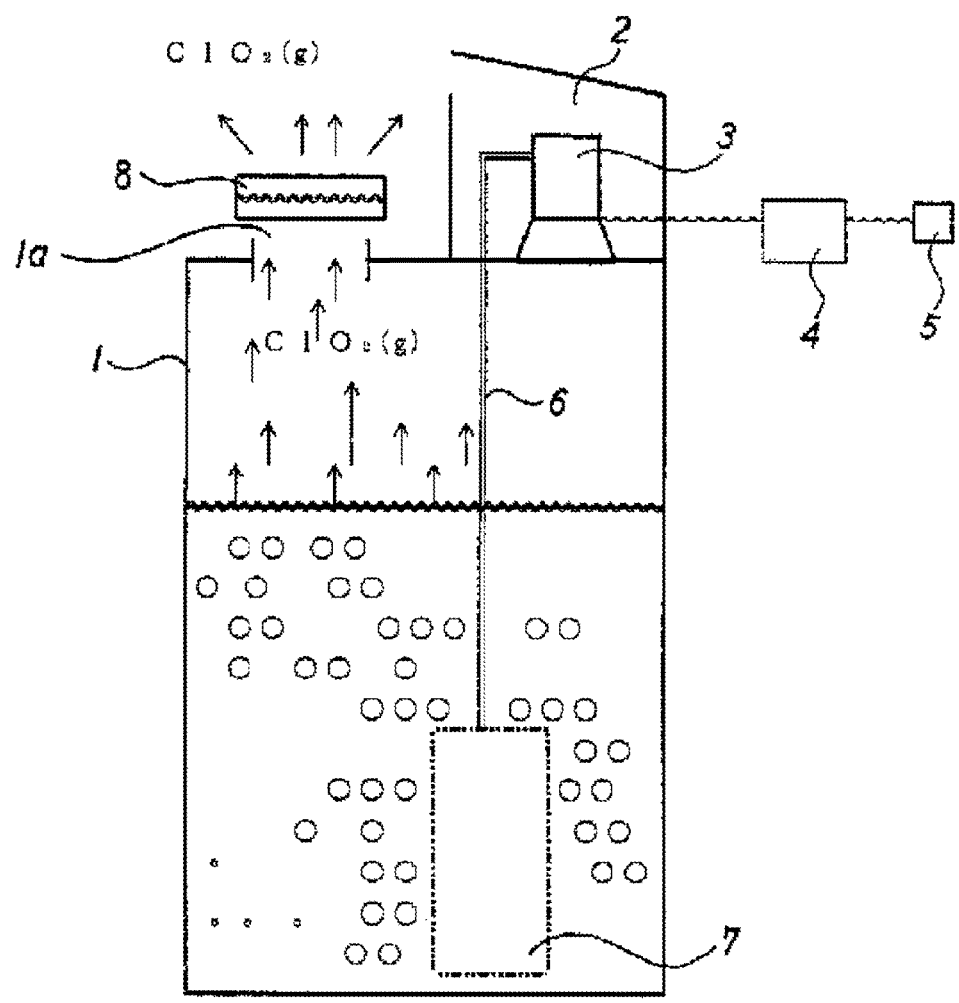
FIG. 8 is a sectional view of the prior art apparatus proposed in JP1998-192377.
Figure 9:
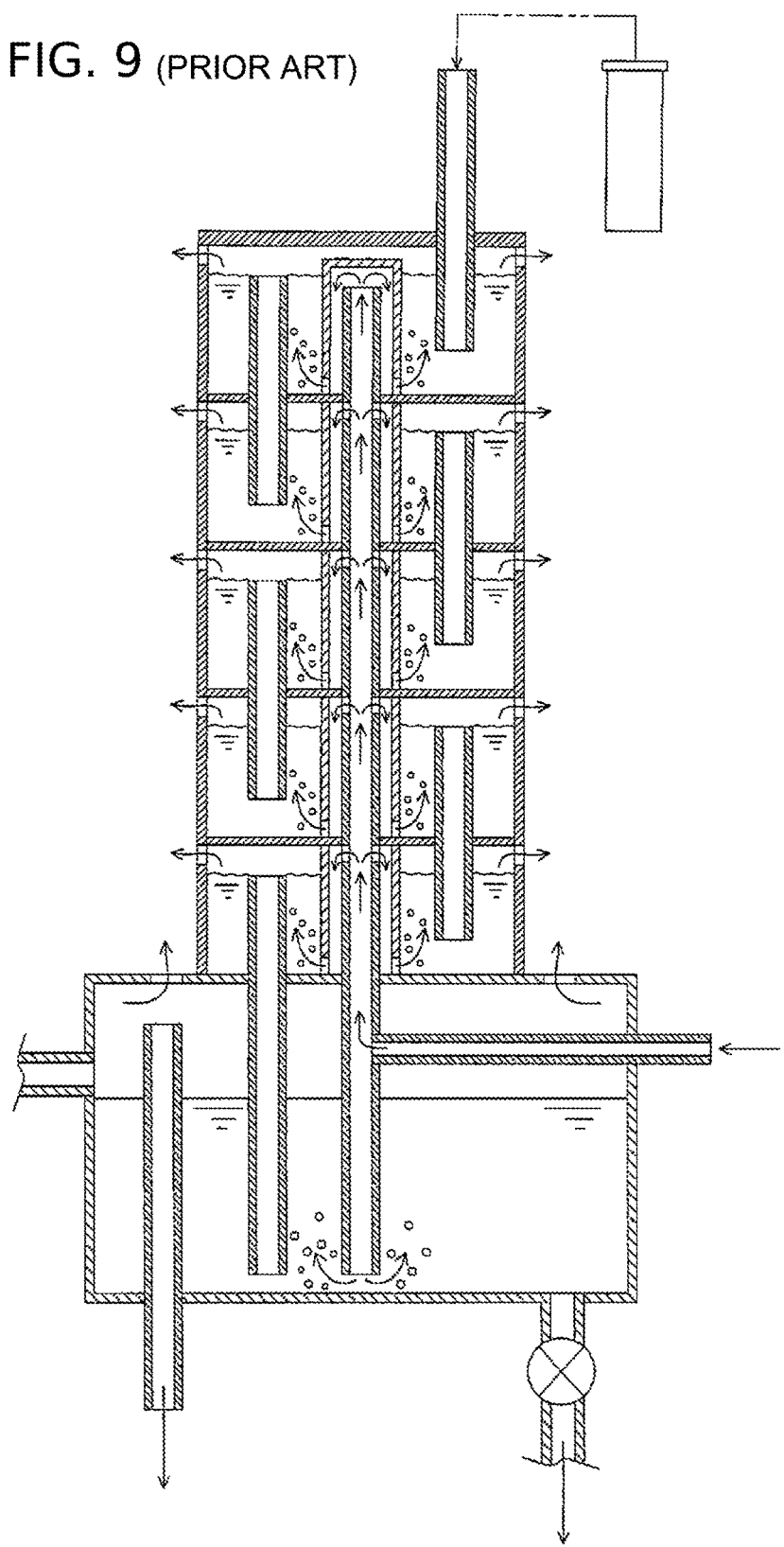
FIG. 9 is a sectional view of the prior art apparatus proposed in JP5639294.

While various types of reactors can be used as the reactor 10 that makes the first chemical containing chlorite and the second chemical containing acid react with each other, this embodiment employs, as shown in FIGS. 6 and 7, a reactor 10 including a large cylinder 11 in the shape of a cylinder having a bottom surface, which makes up the external shape of the reactor 10, a medium cylinder 12 in the shape of a cylinder having a bottom surface and housed within the large cylinder 11, and a small cylinder 13 in the shape of a cylinder having a bottom surface and housed within the medium cylinder 12, in which, as shown in FIG. 6, a first spiral groove 14a is formed between the large cylinder 11 and the medium cylinder 12, and a second spiral groove 14b is formed between the medium cylinder 12 and the small cylinder 13. As shown in FIG. 7, a lid 15 is mounted to the large cylinder 11 which sequentially houses the medium cylinder 12 and the small cylinder 13, the lid 15 securing the medium cylinder 12 and the small cylinder 13 within the large cylinder 11.

As shown in FIGS. 2 and 3, the chemicals in a first chemical tank 16a and a second chemical tank 16b are separately fed to the reactor 10 through chemical transporting pumps 16c. The first and second chemical tanks 16a and 16b respectively contain, for example, 25% sodium chlorite and 9% hydrochloric acid which are fed respectively to a first connection port 11a and a second connection port 11b of the large cylinder 11, as shown in FIG. 6. In other words, the chemicals in the first chemical tank 16a and the second chemical tank 16b are contained separately respectively in the first chemical tank 16a and the second chemical tank 16b, and thus will not accidentally react with each other before they are fed to the reactor 10.

When the chemicals in the first chemical tank 16a and the second chemical tank 16b are fed through the chemical transporting pumps 16c to the connection ports 11a and 11b of the large cylinder 11, the chemicals enter the large cylinder 11 through holes formed in the bottom of the large cylinder 11, and a first mixing step is carried out in collectors 12a of the medium cylinder 12 housed within the large cylinder 11. After this, the chemicals flow through an outlet 12b which communicates with the bottom portion of the medium cylinder 12 and enter the first end of the first spiral groove 14a. The chemicals are then guided by the first spiral groove 14a to flow towards the second end of the first spiral groove 14a. Since the first spiral groove 14a literally is a groove with a spiral shape, it can for example have a total length several times the height of the large cylinder 11. The first spiral groove 14a carries out a second mixing step of the inflowing chemicals. The first and second mixing steps cause a reaction of the chemicals, starting generation of a given amount of chlorine dioxide solution 30a.

When the chemicals containing the chlorine dioxide solution 30a have flowed to the second end of the first spiral groove 14a, they enter the medium cylinder 12 through a communication port 12c formed at the second end of the first spiral grove 14a, and flow into the first end of the second spiral groove 14b formed on the surface of the small cylinder 13 which is housed within the medium cylinder 12. Then, the chemicals including the chlorine dioxide solution 30a flow through the second spiral groove 14b towards its second end (the lower end in this embodiment) and a third mixing step is carried out, whereby more chlorine dioxide solution 30a is generated from the remaining chemicals.

When the chemicals containing the chlorine dioxide solution 30a (at this stage the chemicals have almost completed their reaction and can be considered to completely consist of chlorine dioxide solution 30a) have reached the second end of the second spiral groove 14b, they will reach the lower end of a center cavity 13a through a connection port 13b formed at the lower end of the small cylinder 13, rise up through the center cavity 13a while undergoing further mixing, and then be discharged through the outlet 15a of the lid 15. At this time, the chemicals have completely become the chlorine dioxide solution 30a.

As a result, generation of the chlorine dioxide solution 30a in the reactor 10 will not occur unless the chemicals are fed into the small space constituting this reactor 10, which means that not only will there not be any accidental generation of the chlorine dioxide gas 30b, but also that by controlling the feeding of the chemicals, the amount of gas and time of generation can be controlled. Due to the presence of this reactor 10, the chlorine dioxide gas generator 100 according to an embodiment of the present invention can be made much smaller and compact than for example the apparatus proposed in JP1998-192377.

The generated chlorine dioxide solution 30a is transported from the outlet 15a of the lid 15, which seals the interior of the reactor 10, to a separation tank 20 through a hose or the like, and the chlorine dioxide gas 30b is separated in this separation tank 20. The separated chlorine dioxide gas 30b is then sprayed into the enclosed space 40 by the chlorine dioxide gas generator 100, as shown in FIG. 1.

Figure 4:
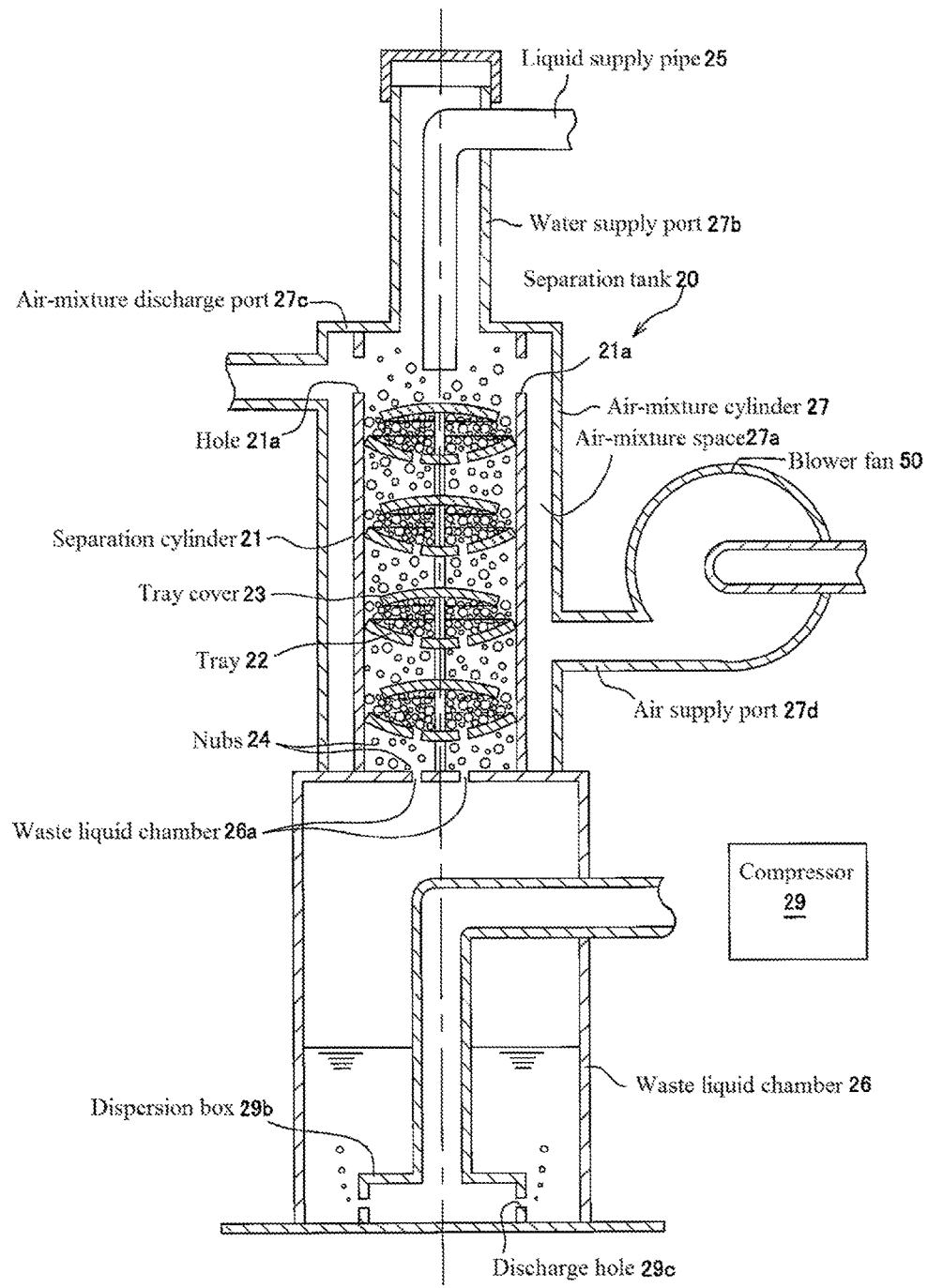
FIG. 4 is an enlarged partial cross-sectional view of the separation tank 20.

As shown in FIG. 4, the separation tank 20 according to the present embodiment includes a separation cylinder 21, trays 22, tray covers 23, nubs 24, a liquid supply pipe 25, and an air-mixture cylinder 27. The separation cylinder 21 is fed from below with air fed from holes 26a of a waste liquid chamber 26 via a compressor 29, and from above with chlorine dioxide solution 30a from the liquid supply pipe 25 of the reactor 10, or with washing water from a water supply port 27b described later.

The separation cylinder 21 constituting the separation tank 20 is provided standing on top of the waste liquid chamber 26, and has holes 21a at its upper portion. The separation cylinder 21 supports the trays 22 and tray covers 23 described later, and houses the nubs 24. In the present embodiment, the trays 22 and tray covers 23 are supported at equal intervals by a central supporting rod, as shown in FIG. 4, and the housed nubs 24 are arranged in uniform amounts between each tray 22 and respective tray cover 23.

The central supporting rod that supports the trays 22 and tray covers 23 may be implemented by replacing the supporting rod with a pipe having a closed upper end and a bottom end communicating with the waste liquid chamber 26, the side of the pipe inside the separation cylinder 21 having a plurality of holes for communication between the interior of the pipe and the interior of the separation cylinder 21. The central pipe that supports the trays 22 and tray covers 23 can thus feed air from the interior of the pipe into the separation cylinder 21 through the holes, and can allow chlorine dioxide solution 30a to flow around the pipe, enabling efficient separation of chlorine dioxide gas 30b from the chlorine dioxide solution 30a.

Figure 5:
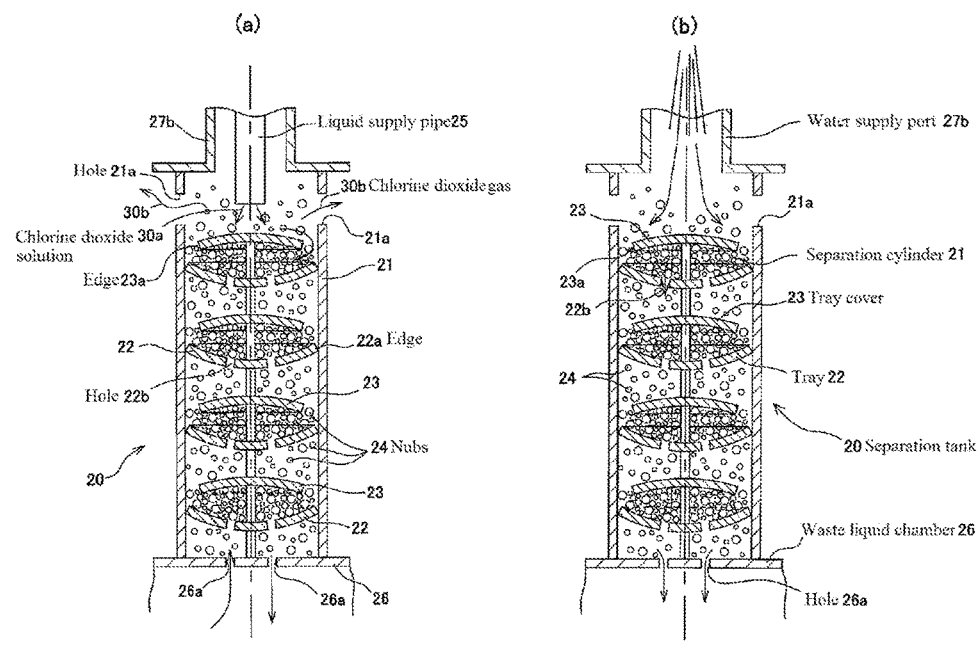
FIG. 5 is an enlarged view of a separation cylinder of the separation tank 20 shown in FIG. 4, where (a) is an enlarged cross-sectional view showing separation and dilution of chlorine dioxide gas 30b, and (b) is an enlarged cross-sectional view showing water washing of the interior of the separation cylinder 21.

As shown in FIGS. 5 (a) and (b), the lower side of the interior of the separation cylinder 21 is fed with air from the holes 26a of the waste liquid chamber 26 via the compressor 29, and this air rises through a series of complex passages formed by the holes 22 of the trays 22, the gaps between the nubs 24, and the passages between the edges 23a of the tray covers 23 and the inner surface of the separation cylinder 21. Meanwhile, as described above, the upper side of the interior of the separation cylinder 21 is fed with the chlorine dioxide solution 30a from the liquid supply pipe 25 of the reactor 10, or with washing water from the water supply port 27b. The chlorine dioxide solution 30a or washing water flows downwardly onto the top surfaces of the tray covers 23, passes through the passages between the edges 23a of the tray covers 23 and the inner surface of the separation cylinder 21 and the gaps between the nubs 24 and is caught in the trays 22, and then flows further down through holes 22b of the trays 22 until it finally flows into the waste liquid chamber 26 through the holes 26a.

The waste liquid chamber 26 upon which the separation cylinder 21 stands has holes 26a at its center, which are enclosed by the separation cylinder 21, such that air fed into the waste liquid chamber 26 cannot exit the waste liquid chamber 26 other than through the holes 26a into the separation cylinder 21. The waste liquid chamber 26 may be of any configuration so long as it fulfills this function.

In order to achieve the functionality described above, as shown in FIGS. 5 (a) and (b), each tray 22 is of a downwardly convex shape and has an edge 22a connected to the inner surface of the separation cylinder 21 and holes 22b at its center. The trays 22 are made in this downwardly convex shape in order to allow for accumulation of up to a certain amount of chlorine dioxide solution 30a or washing water provided from above, and gather the accumulated chlorine dioxide solution 30a or washing water in the center to let it flow down through the holes 22b. These holes 22b are provided at the center of the tray 22 in order to make the chlorine dioxide solution 30a or washing water caught by the tray 22 flow down through the holes 22b onto the center of the top surface of the below tray cover 23 and create the longest possible flow path through the passage between the edge 23a of the tray cover 23 and the inner surface of the separation cylinder 21, so as maximize the contact time and area of the chlorine dioxide solution 30a with the air, or the washing water with the surfaces of each member.

Further, as shown in FIGS. 5 (a) and (b), each tray cover 23 is located at a predetermined distance from each tray 22, and is of an upwardly convex shape having and edge 23a separated from the inner surface 21 of the separation cylinder 21 to form a passage. The tray covers 23 are made in this upwardly convex shape in order to make the chlorine dioxide solution 30a or washing water flow into the passage formed between the edge 23a of the tray cover 23 and the inner surface of the separation cylinder 21, so as to maximize the contact time and area of the chlorine dioxide solution 30a with the air, or the washing water with the surfaces of each member.

As shown in FIGS. 5 (a) and (b), the nubs 24 packed between the tray covers 23 and respective trays 22 make the flow path of the chlorine dioxide solution 30a or the washing water as long and complex as possible, and can be made of a material that is not corroded by the chlorine dioxide solution 30a or chlorine dioxide gas 30b, for example thin metal pieces or Teflon™.

Further, as shown in FIG. 4, the top of the interior of the separation cylinder 21 configured as described above is in communication with the liquid supply pipe 25 of the reactor 10 and the water supply port 27b that feeds washing water from a water supply not shown here, allowing for chlorine dioxide solution 30a or washing water to be fed into the separation cylinder 21.

The air-mixture cylinder 27 is provided on top of the waste liquid chamber 26 and around the separation cylinder 21. This air-mixture cylinder 27 forms an air-mixture space 27a around the separation cylinder 21. At the top end of the air-mixture cylinder 27 there is formed the aforementioned water supply port 27b, and at the sides of the air-mixture cylinder 27 there are formed an air-mixture discharge port 27c and an air supply port 27d which feeds air from a blower fan 50. In other words, when chlorine dioxide gas 30b that has been separated from the chlorine dioxide solution 30a in the separation cylinder 21 is fed into the air-mixture space 27a through the holes 21a formed at the upper portion of the separation cylinder 21, the air-mixture cylinder 27 allows the chlorine dioxide gas 30b to be diluted with air fed into the air-mixture space 27a from the air supply port 27d of the blower fan 50 and fed into the enclosed space 40 through the air-mixture discharge port 27c formed at the side of the air-mixture cylinder 27.

In the chlorine dioxide gas generator 100 according to the present embodiment, the aforementioned air-mixture cylinder 27 and the separation cylinder 21 housed within it are provided on the waste liquid chamber 26. As shown in FIGS. 3 and 4, outside air can be fed into the waste liquid chamber 26 from the compressor 29 through a supply pipe 29a. The end of the supply pipe 29a is connected to a dispersion box 29b provided at the lower end of the waste liquid chamber 26, the dispersion box 29b being provided with discharge holes 29c for feeding air into the waste liquid chamber 26.

As such, air is forcibly fed into the waste liquid chamber 26 according to the present embodiment from the external compressor 29, whereby the air that is fed into the dispersion box 29b through the supply pipe 29a is discharged into the waste liquid chamber 26 through the discharge holes 29c. Since the waste liquid chamber 26 collects chlorine dioxide solution 30a from which most of the chlorine dioxide gas 30b has been separated as waste liquid, the air provided by the compressor 29 will rise up through the waste liquid, causing bubbling. If there is any trace of chlorine dioxide gas 30b left to be separated from the waste chlorine dioxide 30a, the remaining chlorine dioxide gas 30b will be separated by this bubbling process.

This separated chlorine dioxide gas 30b is fed into the separation cylinder 21 along with the separation air provided by the compressor 29 through the holes 26a of the waste liquid chamber 26, joins the chlorine dioxide gas 30b separated from the chlorine dioxide solution 30a, and can be used for fumigation.

Further, as shown in FIG. 3, the waste liquid chamber 26 is provided with a drain pipe 28, and by opening a drain valve 28a, waste liquid collected in the waste liquid chamber 26 can be discharged from a drain 28b into an external container or treatment facility not shown here.

In order to separate chlorine dioxide gas 30b from the chlorine dioxide solution 30a in the chlorine dioxide gas generator 100 configured as described above, specific materials are fed into the reactor 10 to continuously generate chlorine dioxide solution 30a, this chlorine dioxide solution 30a is fed into the separation tank 20 through the liquid supply pipe 25, and the compressor 29 is activated to feed air into the waste liquid chamber 26, which air is fed into the separation tank 20 through the holes 26a of the waste liquid chamber 26. In other words, chlorine dioxide 30a is fed into the separation tank 20 from above while, at the same time, air for separating and diluting chlorine dioxide gas 30b from the chlorine dioxide solution 30a is fed into the separation tank 20 from below.

Further, in order to wash the interior of the separation tank 20 of the chlorine dioxide gas generator 100, washing water is fed into the separation tank 20 from the water supply port 27b instead of the chlorine dioxide solution 30a, and air is fed into the separation tank 20 from the waste liquid chamber 26. As a result, any residual chlorine dioxide solution 30a in the trays 22, on the surfaces of the tray covers 23, or in the passages between the nubs 24 can be washed off, and any residual chlorine dioxide remaining in the washed off waste liquid can be separated into the air by way of the complex passages and stimulation by the air.

Since air is also fed by the compressor 29 into the waste liquid in the waste liquid chamber 26 during the aforementioned washing process in a so-called bubbling operation, residual chlorine dioxide in the waste liquid is gasified and fed into the enclosed space 40 via the air-mixture discharge port 27c. Of course, the waste liquid in the waste liquid chamber is later safely treated by an apparatus not shown here to yield waste water that is substantially free of chlorine dioxide.

In the chlorine dioxide gas generator 100 according to the present embodiment, the chemical transporting pumps 16c which feed chemicals from the first and second chemical tanks 16a and 16b, the air pump which feeds air through the air supply pipe to the interior of the inner pipe of the air supply pipe, and the blower fan 50, are controlled by a control panel 60 provided on a portion of the chlorine dioxide gas generator 100. In this case, control is effected by a control system based on received signals from a concentration sensor installed in the enclosed space 40 which senses the concentration of the chlorine dioxide solution 30a, or from a timer etc.

The chlorine dioxide gas generator 100 according to the foregoing embodiment will now be explained referring to a basic example wherein in an enclosed space 40 having a capacity of 450 m$^3$, the concentration of the chlorine dioxide gas 30b is 400 ppm (desired concentration to enable fumigation). Further, the maximum allowable concentration of the chlorine dioxide gas 30b in an enclosed space having a capacity of 450 m$^3$ is twice the desired concentration; 800 ppm, and the amount of chlorine dioxide gas 30b needed to achieve this concentration is 1010 g. Based on these premises, the first chemical tank 16a may be filled with at least 4.5 liters (5.4 kg) of 25% sodium chlorite, and the second chemical tank 16b may be filled with at least 4.7 liters (4.8 kg) of 9% hydrochloric acid.

In other words, a capacity of 10 liters of the first and second chemical tanks 16a and 16b is sufficient in order to make the concentration of the chlorine dioxide gas 30b in an enclosed space 40 having a capacity of 450 m$^3$ be 400 ppm within the time period described below. Further, since the reactor 10 which is fed with chemicals from the first chemical tank 16a and/or the second chemical tank 16b can be made even smaller, the entire chlorine dioxide gas generator 100 can be miniaturized.

By feeding the separation cylinder 21 of the separation tank 20 with air before feeding the chemicals from the first chemical tank 16a and/or the second chemical tank 16b to the reactor as mentioned above, separation of the chlorine dioxide gas 30b can be initiated immediately after the chlorine dioxide solution 30a has been transported from the reactor 10.

With the foregoing preparations finished, the chemicals are fed to the reactor by the chemical transporting pumps 16c in a 1:1 ratio, the chlorine dioxide solution 30a is generated in the reactor in the state described above, the chlorine dioxide gas 30b is separated from the chlorine dioxide solution 30a in the separation tank 20, and the separated chlorine dioxide gas 30b is gradually fed into the enclosed space 40. Under the foregoing conditions, it takes about 30 minutes to one hour until the concentration of the chlorine dioxide gas 30b in the enclosed space 40 becomes 400 ppm.

In order to sufficiently fumigate an enclosed space 40 having a capacity of 450 m$^3$, a state where the concentration of the chlorine dioxide gas 30b in the enclosed space 40 is 300 to 400 ppm needs to be maintained for about three hours. In order to do this, production of chlorine dioxide solution 30a may be carried out intermittently, by intermittently operating the chemical transporting pumps to feed the 25% sodium chlorite in the first chemical tank 16a and the 9% hydrochloric acid in the second chemical tank 16b into the reactor 10.

DESCRIPTION OF THE REFERENCE NUMERALS 100 chlorine dioxide gas generator
10 reactor
11 large cylinder
11a first connection port
11b second connection port
12 medium cylinder
12a collector
12b outlet
12c communication port
13 small cylinder
13a center cavity
13b connection port
14a first spiral groove
14b second spiral groove
15 lid
15a outlet
16a first chemical tank
16b second chemical tank
16c chemical transporting pump
20 separation tank
21 separation cylinder
21a hole
22 tray
22a edge
22b hole
23 tray cover
23a edge
24 nub
25 liquid supply pipe
26 waste liquid chamber
26a hole
27 air-mixture cylinder
27a air-mixture space
27b water supply port
27c air-mixture discharge port
27d air supply port
28 drain pipe
28a drain valve
28b drain
29 compressor
29a supply pipe
29b dispersion box
29c discharge hole
30a chlorine dioxide solution
30b chlorine dioxide gas
40 enclosed space
50 blower fan
60 control panel

What is claimed is:

1. A chlorine dioxide gas generator comprising:
a reactor configured to cause a reaction between a first chemical containing chlorite and a second chemical containing acid; and
a separation tank configured to separate a chlorine dioxide gas from a chlorine dioxide solution generated in the reactor, the chlorine dioxide gas generator being adapted to disinfect an enclosed space by means of the chlorine dioxide gas,
wherein the separation tank comprises:
a separation cylinder provided standing on a waste liquid chamber so as to enclose holes provided at the center of the waste liquid chamber, the separation cylinder having holes at its upper portion;

a plurality of trays having edges connected to an inner surface of the separation cylinder, each of the plurality of trays being of a downwardly convex shape and having holes at its center portion;
a plurality of tray covers, each tray cover being arranged at a predetermined distance from the respective tray, each tray cover being of an upwardly convex shape and having an edge that is separate from the inner surface of the separation cylinder so as to form a passage;
a plurality of nubs arranged between the plurality of trays and the plurality of tray covers;
a liquid supply pipe from the reactor communicating with the upper portion of the separation cylinder; and
an air-mixture cylinder arranged on the waste liquid chamber and configured to form an air-mixture space around the separation cylinder, the air-mixture cylinder having at its top end a water supply port, and having on its sides an air-mixture discharge port and an air supply port configured to supply air from a blower fan.

* * * * *